United States Patent

Wagner

(10) Patent No.: US 9,480,788 B2
(45) Date of Patent: Nov. 1, 2016

(54) MEDICAL INJECTION SYSTEMS AND METHODS RELATED TO USER ACTIVATED CONTROL DEVICES

(71) Applicant: ACIST MEDICAL SYSTEMS, INC., Eden Prairie, MN (US)

(72) Inventor: Reed Brian Wagner, Bloomington, MN (US)

(73) Assignee: ACIST Medical Systems, Inc., Eden Prairie, MN (US)

( * ) Notice: Subject to any disclaimer, the term of this patent is extended or adjusted under 35 U.S.C. 154(b) by 324 days.

(21) Appl. No.: 13/689,966

(22) Filed: Nov. 30, 2012

(65) Prior Publication Data

US 2014/0155742 A1 Jun. 5, 2014

(51) Int. Cl.
*A61M 5/00* (2006.01)
*A61M 5/168* (2006.01)

(52) U.S. Cl.
CPC ......... *A61M 5/007* (2013.01); *A61M 5/16854* (2013.01); *A61M 2205/15* (2013.01); *A61M 2205/353* (2013.01); *A61M 2205/3569* (2013.01); *A61M 2205/502* (2013.01)

(58) Field of Classification Search
CPC ..................... A61M 3/0216; A61M 2205/15; A61M 5/168; A61M 5/16831; A61M 5/16854; A61M 2005/14513; A61M 5/152; A61M 5/31593; A61M 5/31595; A61M 39/227
USPC .................. 604/65, 66, 503, 890.1, 505, 67
See application file for complete search history.

(56) References Cited

U.S. PATENT DOCUMENTS

| | | | |
|---|---|---|---|
| 2,645,224 A * | 7/1953 | Beebe | A61M 5/204 604/183 |
| 5,515,851 A | 5/1996 | Goldstein | |
| 5,916,165 A * | 6/1999 | Duchon | A61M 5/14546 600/431 |
| 6,485,471 B1 * | 11/2002 | Zivitz et al. | 604/212 |
| 6,935,163 B2 * | 8/2005 | Stewart | G01M 3/2815 73/49.7 |
| 8,118,780 B2 | 2/2012 | Fago et al. | |
| 2003/0225380 A1 * | 12/2003 | Redl et al. | 604/289 |

(Continued)

FOREIGN PATENT DOCUMENTS

| | | |
|---|---|---|
| EP | 1843141 A2 | 10/2007 |
| EP | 2158930 A1 * | 3/2010 |
| WO | 9924094 A1 | 5/1999 |

OTHER PUBLICATIONS

International Search Report and Written Opinion for International Application No. PCT/US2013/071799, mailed May 15, 2014, 11 pages.

*Primary Examiner* — Imani Hayman
*Assistant Examiner* — Nilay Shah
(74) *Attorney, Agent, or Firm* — Fredrikson & Byron, P.A.

(57) ABSTRACT

A control module for a medical injection system generates an injection control signal based on sensed internal pressure of a user activated control device, for example, in response to an applied external force that causes the sensed internal pressure to increase from a baseline pressure, and continues to sense the internal pressure of the device, following release of the applied external force, so that, if the sensed internal pressure drops below the baseline pressure, the control module may generate a notification. Thus, an operator of the system may monitor internal pressure of the control device for a drop below the baseline pressure, and then, if such a drop is detected, inspect the control device for leaks and reconnect, replace or repair the control device, or simply reconnect or replace the control device.

21 Claims, 5 Drawing Sheets

(56) References Cited

U.S. PATENT DOCUMENTS

2006/0129084 A1* 6/2006 Miyato .......................... 604/19
2010/0262078 A1* 10/2010 Blomquist .................... 604/151
2010/0331779 A1* 12/2010 Nystrom ............... A61M 5/007
                                                          604/125

* cited by examiner

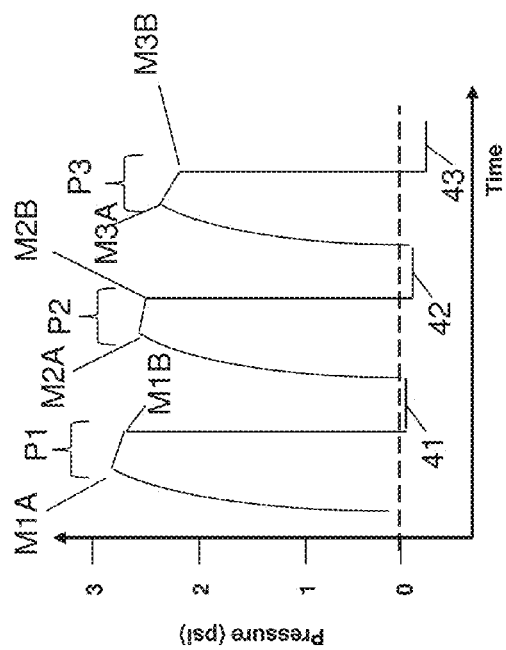
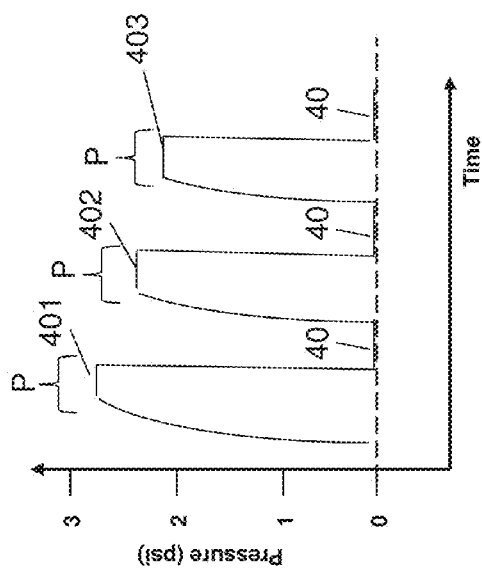
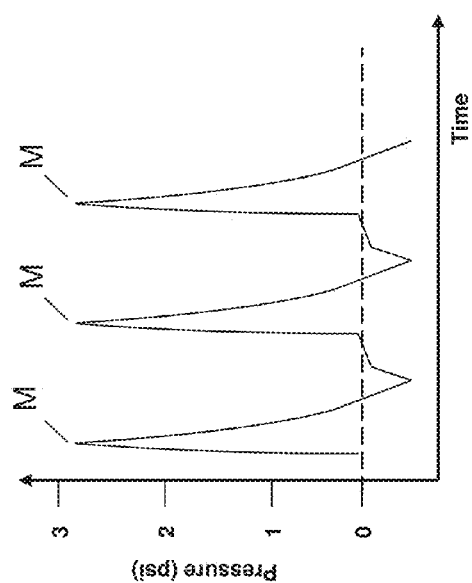

MEDICAL INJECTION SYSTEMS AND METHODS RELATED TO USER ACTIVATED CONTROL DEVICES

TECHNICAL FIELD

The present disclosure pertains to medical injection systems and more particularly to user activated control devices thereof.

BACKGROUND

FIG. 1 is a perspective view of an exemplary medical injection system 100 (the ACIST $CV_i$® system) adapted to deliver fluids, such as a contrast agent and saline, into a patient's vascular system for medical imaging procedures. FIG. 1 illustrates a first fluid reservoir 132 supplying, via a fill tubing line 27-F, a syringe-type positive displacement pump of a pressurizing unit 130, which is coupled to an injector 140 of system 100; an injection tubing line 27-I is shown coupled to unit 130 for injection of the fluid, for example, a radiopaque contrast agent, into a patient's vascular system via an inserted catheter (not shown), for example, that is coupled to a patient tubing line 122 at a connector 120 thereof. FIG. 1 further illustrates a second fluid reservoir 138 from which saline is drawn by a peristaltic pump 106 through yet another tubing line 128 that feeds into tubing line 122, for injection of the saline into the patient. A manifold valve 124 and associated sensor 114 control the flow of fluids into tubing line 122, from pressurizing unit 130 and from tubing line 128.

FIG. 1 further illustrates a pneumatic user activated control device 200, which is coupled via connectors 251, 253 to an injection control module contained within a control panel 152 of system 100. Control device 200 includes a first compressible bladder 210, which is coupled to, and in fluid communication with a first tubing line 201, and a second compressible bladder 230, which is coupled to, and in fluid communication with a second tubing line 203. Each tubing line 201, 203 is coupled to a corresponding pressure sensor of the injection control module, so that, in response to an external force applied by a user/operator to the corresponding bladder 210, 230, an injection control signal can be generated for the positive displacement pump of pressurizing unit 130 and peristaltic pump 106, respectively, according to the sensed pressure of the corresponding line 201, 203. Control device 200 is preferably calibrated so that an amount of force, above a predetermined threshold, that the operator applies to bladder 210 is proportional to a volume and rate of contrast injected via pressurizing unit 130. Such a control device is described in commonly assigned U.S. Pat. No. 5,916,165. The efficient injection of contrast agent into a patient over the course of an imaging procedure relies on responsive user activated control devices, such as device 200.

SUMMARY

Medical injection systems of the present invention include a pump, an injection control module, and a user activated control device coupled to the injection control module, wherein the control module includes a pressure sensor in fluid communication with an internal volume of the control device, to sense an internal pressure thereof, so that the control module may generate an injection control signal, which is based upon the sensed internal pressure of the control device; the sensed internal pressure increases from a baseline pressure in response to application of an external force to the control device. According to some embodiments and methods of the present invention, the pressure sensor continues to sense the internal pressure of the control device following release of the applied external force, and, if the sensed internal pressure drops below the baseline pressure, the control module generates a notification. Thus, according to some methods, a user/operator of the system, during setup/calibration and/or system operation, can monitor the sensed internal pressure of the control device, after releasing an applied external force to the control device, to detect if the sensed internal pressure drops below the baseline pressure; and, if the internal pressure does drops below the baseline pressure, the operator may then inspect the control device for leaks and repair, reconnect or replace the control device, or simply reconnect or replace the control device without inspecting. According to some methods and embodiments, the baseline pressure is approximately atmospheric pressure, or, preferably, zero differential pressure with respect to atmospheric.

BRIEF DESCRIPTION OF THE DRAWINGS

The following drawings are illustrative of particular methods and embodiments of the present disclosure and, therefore, do not limit the scope of the invention. The drawings are not to scale (unless so stated) and are intended for use in conjunction with the explanations in the following detailed description. Methods and embodiments will hereinafter be described in conjunction with the appended drawings, wherein like numerals denote like elements, and:

FIGS. 4A-C present exemplary plots of pressure versus time, which may be generated according to some methods and embodiments of the present invention.

DETAILED DESCRIPTION

The following detailed description is exemplary in nature and is not intended to limit the scope, applicability, or configuration of the invention in any way. Rather, the following description provides practical illustrations for implementing exemplary methods and embodiments. Those skilled in the art will recognize that many of the examples provided have suitable alternatives that can be utilized.

Figure 1:
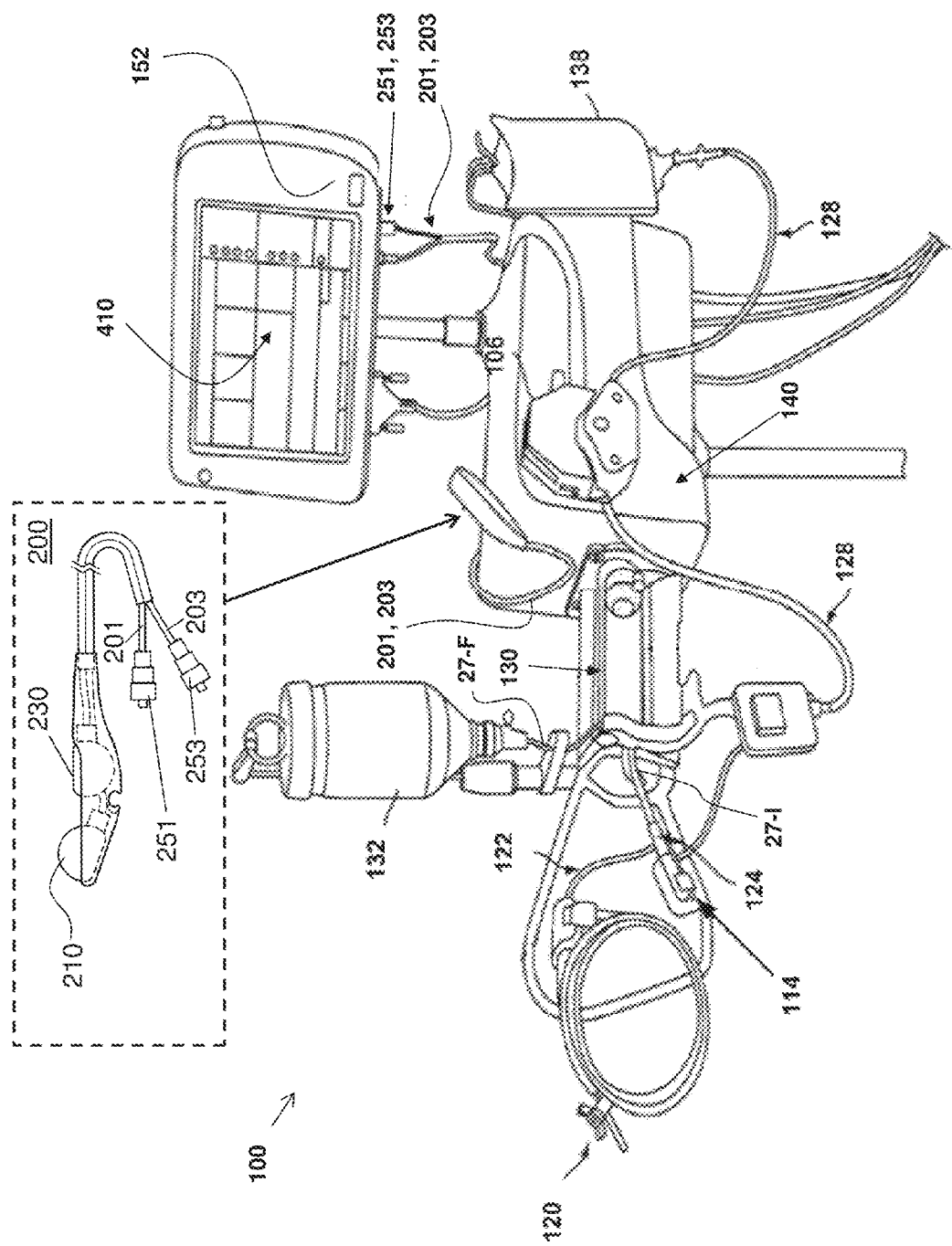
FIG. 1 is a perspective view of an exemplary medical injection systems, with an enlarged detailed view of a user activated control device thereof, according to some embodiments.
Figure 2:
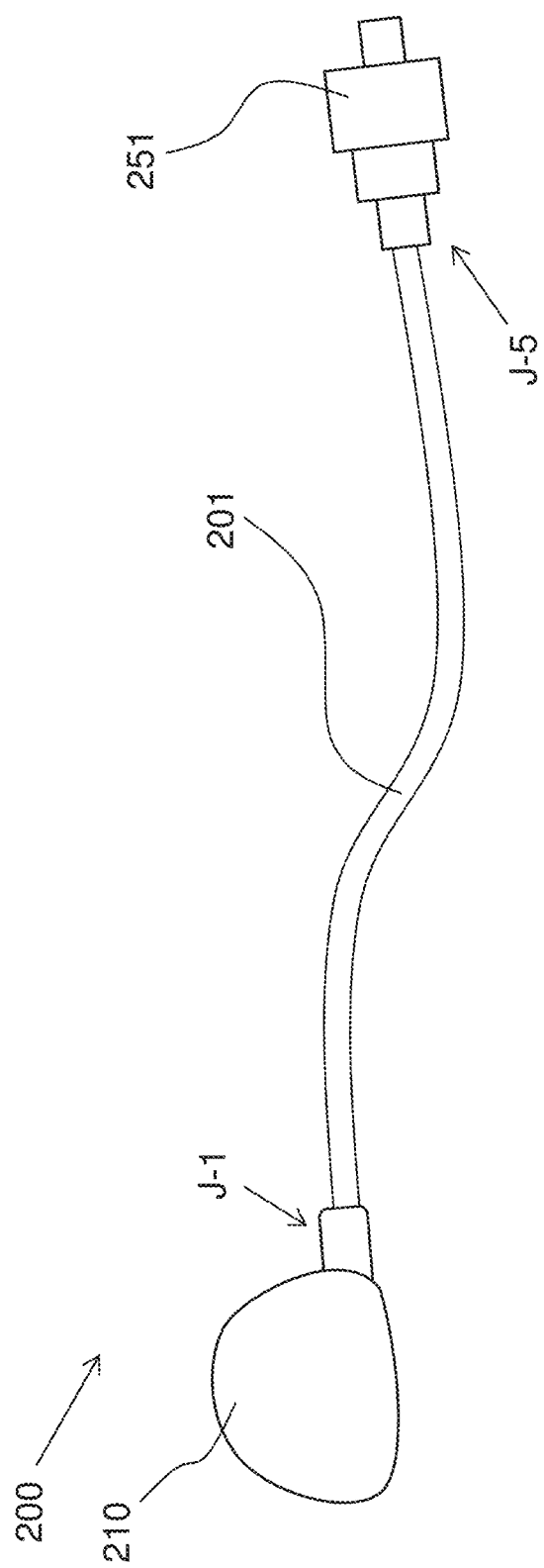
FIG. 2 is a plan view of a portion of the control device, according to some embodiments.

FIG. 2 shows a portion of user activated control device 200 of system 100 (FIG. 1), which is employed for controlling contrast injections via the positive displacement pump of pressurizing unit 130. FIG. 2 illustrates bladder 210 coupled to tubing line 201, which is terminated by connector 251, for example, a Luer type, that couples the compressible volume of bladder 210 in fluid communication with a pressure sensor 315 of an injection control module 300, for example, as represented by the functional block diagram of FIG. 3. With reference back to FIG. 1, control module 300 may be contained in control panel 152 of system 100. Alternately, with further reference to FIG. 1, control module 300 may be housed with injector 140 and mating fittings for connectors 251, 253 mounted thereon, rather than on control panel 152. The aforementioned U.S. Pat. No. 5,916,165, which is hereby incorporated by reference, describes suitable constructions, materials, and dimensions for devices like device 200, that employ bladders coupled to tubing lines, like bladder 210 and tubing line 201.

Figure 3:
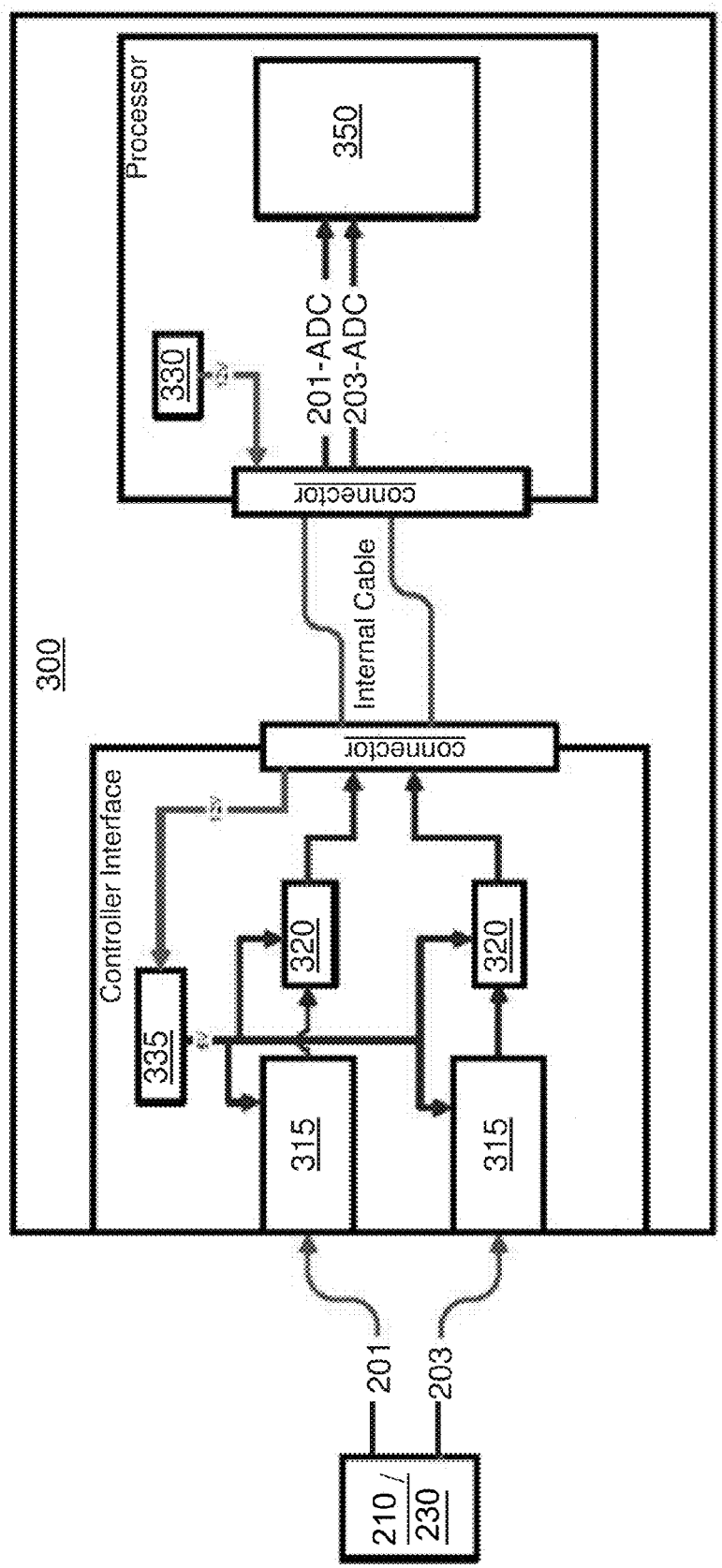
FIG. 3 is a functional block diagram for an injection control module, according to some embodiments.

FIG. 3 illustrates injection control module 300 configured on a controller interface board and a processor board, which are coupled to one another via an internal cable, according to some embodiments. The controller interface is shown receiving input from a connected user activated control device, which may be a hand-held device, for example, device 200 (FIGS. 1 and 2), or of any other suitable configuration allowing a user to apply an external force in a controlled fashion. The controller interface is also shown including two pressure sensors 315, one coupled to each tubing line 201, 203, so as to be in fluid communication with the internal volume of the corresponding bladder 210, 230, to monitor the internal pressures thereof and generate pressure signals for each, which are transmitted through a corresponding conditioning circuit (attenuator/filter/buffer) 320, and then to a microprocessor 350 as ADC input signals 201-ADC, 203-ADC. Microprocessor 350 generates, from input signals 201-ADC and 203-ADC, injection control signals, for example, direct motor control signals or communication to a motor controller for each of the positive displacement pump of pressurizing unit 130 and peristaltic pump 106 (FIG. 1). FIG. 3 further illustrates module 300 including a 12V regulator 330 supplying power to a 5V precision reference 335 for powering pressure sensors 315 within their required voltage specification limits.

A setup/calibration procedure for control device 200 correlates each ADC input signal 201-ADC, for example, resulting from an external force, above a predetermined threshold, applied to bladder 210, to a corresponding injection control signal, each of which dictates a volume flow rate for injection of contrast agent, for example, delivered by the positive displacement pump of pressurizing unit 130. Some setup/calibration methods of the present invention are described below in conjunction with FIG. 5; but first, with reference to FIG. 4A, an exemplary plot of sensed internal pressure (psi) vs. time, which results from the application of three different external forces to bladder 210, is shown. FIG. 4A illustrates three different maximum internal pressures 401, 402, 403, each of which corresponds to a different applied external force, held for a period of time P, and each of which generates a corresponding injection control signal. For example, first pressure 401 corresponds to a control signal that directs the pump of pressurizing unit 130 to deliver a contrast injection at a first volume flow rate, second pressure 402 corresponds to a control signal that directs the pump of pressurizing unit 130 to deliver a contrast injection at a second volume flow rate, which is lower than the first, and third pressure 403 corresponds to a control signal that directs the pump of pressurizing unit 130 to deliver a contrast injection at a third volume flow rate, which is lower than the second. FIG. 4A further illustrates the internal pressure returning to a baseline pressure 40, which may be approximately atmospheric pressure, or, preferably, zero differential pressure with respect to atmospheric, in between each external application of force. Each of the different volume flow rates for contrast agent injection may be desired throughout the course of an imaging procedure, depending on the situation.

With reference back to FIG. 2, it may be appreciated that, in some instances, user activated control device 200 has potential to leak, for example, at a junction J-1 between tubing line 201 and bladder 210, at a junction J-5 between tubing line 201 and fitting 251, or at the connection between fitting 251 and a mating fitting of a housing that contains injection control module 300, for example, control panel 152 or injector 140 (FIG. 1). A leak at one or both of junctions J-1, J-5 may result from forces applied to tubing line 201, which cause partial separation of line 201 from bladder 210 and/or from fitting 251; and, a more probable leak, between fitting 251 and the mating fitting, may be caused by damage to one or both of the fittings, for example, by over-tightening when coupling fitting 251 to the mating fitting, and/or by incomplete coupling of the fittings together, for example, by misaligning the fittings during coupling. An elastic nature of bladder 210 can facilitate leak detection, according to some embodiments and methods of the present invention, since a vacuum is momentarily created within device 200, after the external force is released and bladder 210 draws in air through a leak path when rebounding toward its initial, uncompressed internal volume.

FIG. 4B is an exemplary plot of sensed internal pressure (psi) versus time, in response to three external forces applied to bladder 210, when one or more fairly significant leaks are present in control device 200, for example as previously described. FIG. 4B illustrates an almost instantaneous significant drop in internal pressure from a maximum M (i.e. greater than approximately 10%), for each applied external force, and then a drop in internal pressure below the baseline pressure, upon release of the applied external force, due to a brief vacuum created within device 200. A user would likely detect such a large leak in device 200, either tactilely by the applied force to bladder 210, or visually or audibly by the response of pressurizing unit 130 to halt/abort an initiated injection, or visually by fluoroscopic monitoring of the resulting aborted contrast injection. However, a smaller leak in device 200, which may gradually become larger, for example, as illustrated by the plot of FIG. 4C, may not be so readily detected by a user/operator.

FIG. 4C is an exemplary plot of sensed internal pressure (psi) versus time, which results from the application of three external forces applied to bladder 210, when a relatively small leak exists in user activated control device 200. FIG. 4C illustrates a first sensed maximum internal pressure M1A, in response to a first user applied external force, decaying by a relatively small amount, to a pressure M1B, over a first period of time P1, and then, when all external force is released, dropping to a pressure 41 that is slightly below the baseline pressure, which is zero differential pressure, with respect to atmospheric, in this instance. Subsequently, when the user/operator applies second and third external forces, second and third sensed maximum internal pressures M2A, M3A, each drop a bit more significantly over respective periods P2, P3, to respective pressures M2B, M3B. The drops in the sensed maximum internal pressures, from M1A to M1B, from M2A to M2B, and from M3A to M3B, may each be due to the user/operator slowly releasing applied external force over respective periods P1, P2, P3, or may be due to a leak in system 200 that causes internal pressures to decay when a constant external force is applied over each period P1, P2, P3. But, with further reference to FIG. 4C, it may be appreciated that, each drop of internal pressure below the baseline pressure, for example, to pressures 41, 42, 43, when the user/operator releases the external force each time, provides a more definitive indication of a leak.

Thus, according to embodiments and methods of the present invention, pressure sensor 315 of control module 300 (FIG. 3) senses the internal pressure of control device 200 from the initial connection thereof, when pressure is at a baseline pressure, for example, approximately atmospheric pressure, or zero differential pressure with respect to atmospheric, and throughout calibration/setup and system operation to not only monitor rises in internal pressure from the baseline, in response to external applied forces, but also to monitor falling internal pressures, after the user/operator releases applied external forces, to detect if the internal pressure drops below the baseline pressure. Any detected drop of internal pressure below the baseline pressure can indicate a leak in control device 200. According to an exemplary embodiment, pressure sensor has a range of at least +/−15 psi, and a sensitivity of approximately 0.01 psi, to detect such a drop in the internal pressure of the connected control device. An example of a suitable pressure sensor is the Honeywell SSCyxxNo15PDAA5 Differential Pressure Sensor, wherein 'yxx' designates a variety of available package and port configurations.

With reference back to FIG. 3, according to some embodiments, microprocessor 350 of control module 300 may process input signals 201-ADC to generate and display plots similar to those shown in FIGS. 4A-C, for example, on a monitor 410 of control panel 152 (FIG. 1), as one means for providing notification of a leak in control device 200 to a user/operator of system 100. Alternately, microprocessor 350 may generate simpler visual notification, for example, in the form of a light signal or message on monitor 410, and/or an audible notification signal, when input signal 201-ADC corresponds to a sensed internal pressure of device 200 that has dropped below the baseline pressure. In response to notification, the user/operator may simply replace control device 200, or may first inspect control device 200 for leaks. With reference back to FIG. 2, if one of joints J-1, J-5 is found to be leaking, the user can repair or replace control device 200. Alternately, if the coupling/connection between fitting 251 and the mating fitting of the housing that contains control module 300 is found to be leaking, the user may reconnect fitting 251 to form a leak tight connection.

Figure 5:
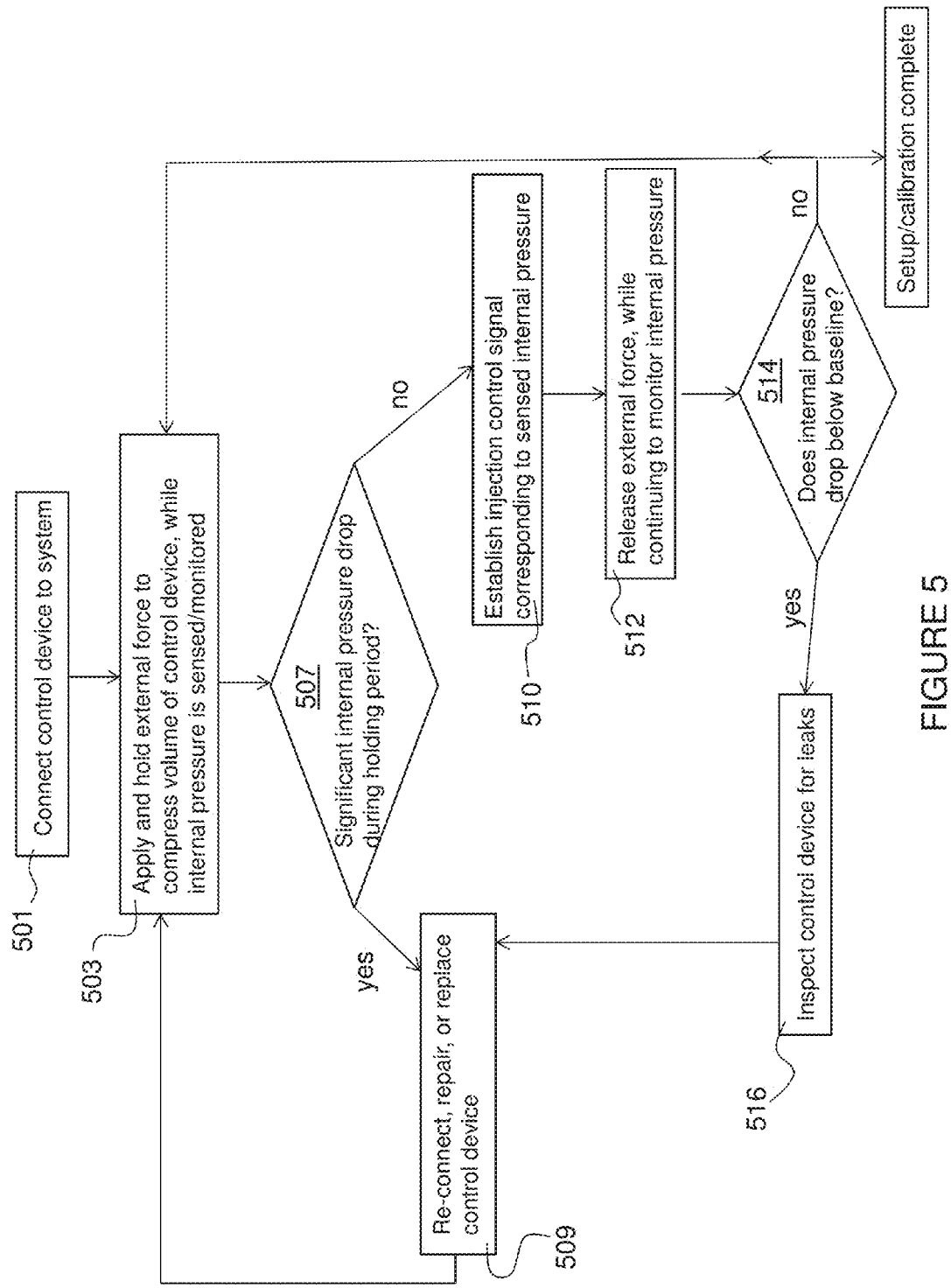
FIG. 5 is a flow chart outlining some methods of the present invention.

FIG. 5 is a flow chart outlining some methods of the present invention, for example, useful in the setup/calibration of a user activated control device for a medical injection system, such as control device 200 in system 100. When the control device is connected to the system, per step 501, an initial, baseline pressure within the control device may be approximately atmospheric pressure, or, preferably, zero differential pressure with respect to atmospheric; alternately, a slightly elevated baseline pressure may be created within the control device. Once connected, a user/operator applies external force to compress the internal volume of the control device, per step 503, and holds the external force while the internal pressure of the device is sensed/monitored; and, per decision point 507, if there is no significant drop in the internal pressure (i.e. greater than approximately 10%) during the holding period, an injection control signal is established (or generated during system operation following setup/calibration) to correspond to the sensed internal pressure, per step 510. Otherwise, if a significant drop in the internal pressure is detected during the holding period, at decision point 507, there is likely a significant leak in the control device such that the control device needs to be replaced, repaired or reconnected, per step 509, after which the setup/calibration may be restarted at step 503. Following step 510, the user/operator releases the external force on the control device, while continuing to monitor the internal pressure of the device, per step 512, for example, via the above described pressure sensor 315 of injection control module 300, whose signals may be processed, as described above, to generate a notification of some sort, if necessary; and, per decision point 514, if the internal pressure drops below the baseline pressure, the user/operator inspects the control device for leaks, per step 516, then reconnects, repairs or replaces the control device, per step 509, and then restarts the setup/calibration at step 503. Alternately, the user may just reconnect or replace the control device, skipping step 516, according to some methods. Otherwise, if the internal pressure of the control device does not drop below the initial baseline pressure, at decision point 514, the setup/calibration is either complete, or may continue at step 503.

According to some methods, the first applied external force, per step 503, following connection of the control device at step 501, is a maximum force for the particular user/operator, and, as the external force is increased from an initial force to the maximum force, internal pressure is continuously monitored to establish a series of injection control signals corresponding to each external applied force in a range from a predetermined threshold force to the maximum. Alternately the user/operator may apply, in a serial manner, individual forces of different magnitudes, per repeated steps 503, to calibrate injection control signals. It should be noted that methods of the present invention are not limited to setup/calibration of user activated control devices, but, as described above, are also implemented during system operation following setup/calibration.

In the foregoing detailed description, the invention has been described with reference to specific embodiments. However, it may be appreciated that various modifications and changes can be made without departing from the scope of the invention as set forth in the appended claims.

I claim:

1. A method for setting up a user activated control device in a medical injection system, the control device having been coupled to a control module of the system via a connection between a tubing line of the control device and a control panel containing the control module, the tubing line being in fluid communication with an internal volume of the control device, the control module including a pressure sensor in fluid communication with the connected tubing line, wherein the internal volume of the control device, the tubing line, and the pressure sensor are included in a closed internal volume intended to prevent fluid from flowing out of the closed internal volume, and the method comprising:

applying an external force to an elastic portion of the control device, to compress the internal volume thereof from a first volume to a second volume, and holding the external force for a period of time, the applied external force increasing an internal pressure of the control device from an initial baseline pressure;

monitoring the internal pressure of the control device during the period of time, the internal pressure being sensed by the pressure sensor of the control module;

if the monitored internal pressure does not significantly drop during the period of time, establishing an injection control signal to correspond to the monitored internal pressure;

releasing the applied external force to allow the elastic portion to rebound to the first volume while continuing to monitor the internal pressure; and if the internal pressure drops below the baseline pressure, after releasing the applied external force, inspecting the control device for leaks in the closed internal volume, wherein the baseline pressure is zero differential pressure with respect to atmospheric.

2. The method of claim 1, wherein inspecting the control device comprises checking the connection of the tubing line of the control device to the control module.

3. The method of claim 1, wherein monitoring the internal pressure of the control device comprises looking for a visual notification generated from signals received from the pressure sensor of the control module.

4. The method of claim 1, wherein monitoring the internal pressure of the control device comprises listening for an audible notification, the audible notification being generated in response to signals received from the pressure sensor of the control module, when the internal pressure drops below the baseline pressure.

5. A method for controlling a medical injection system, the method comprising:
sensing an internal pressure of a compressible internal volume of a control device having an elastic portion, the compressible internal volume being a closed volume intended to prevent fluid from flowing out of the compressible internal volume, the control device being coupled to the system, the internal pressure being greater than a baseline pressure, and the internal pressure being in response to an external force applied to the elastic portion of the control device by an operator of the system to compress the internal volume from a first volume to a second volume;
generating an injection control signal based upon the internal pressure;
continuing to sense the internal pressure of the control device after release of the applied external force and a rebounding of the elastic portion to the first volume; and
generating a notification, if the sensed internal pressure drops below the baseline pressure after the release of the applied external force.

6. The method of claim 5, wherein the notification comprises a visual signal.

7. The method of claim 5, wherein the notification comprises an audible signal.

8. The method of claim 5, wherein the notification comprises an indication of a leak in the compressible internal volume.

9. A method for controlling a medical injection system, the method comprising:
applying an external force to an elastic portion with a compressible closed internal volume of a control device, the control device being coupled to the injection system, the external force compressing the closed internal volume from a first volume to a second volume and increasing an internal pressure of the closed internal volume from a baseline pressure, and the internal pressure being sensed to generate an injection control signal based upon the internal pressure;
releasing the applied external force to allow the elastic portion to rebound to the first volume; and
monitoring if the sensed internal pressure drops below the baseline pressure after the release of the applied external force.

10. The method of claim 9, wherein monitoring the sensed internal pressure comprises listening for an audible notification.

11. The method of claim 9, wherein monitoring the sensed internal pressure comprises looking for a visual notification.

12. The method of claim 9, further comprising inspecting the control device for leaks in the closed internal volume, if the monitored sensed internal pressure drops below the baseline pressure.

13. The method of claim 12, wherein inspecting the control device comprises checking a connection of the device to the system.

14. The method of claim 12, wherein inspecting the control device comprises checking junctions within the device.

15. The method of claim 9, further comprising replacing the control device, if the monitored sensed internal pressure drops below the baseline pressure.

16. The method of claim 9, further comprising reconnecting the control device, if the monitored sensed internal pressure drops below the baseline pressure.

17. The method of claim 9, wherein the baseline pressure is zero differential pressure with respect to atmospheric.

18. A medical injection system comprising a pump, a fluid reservoir configured to hold a fluid for injecting into a patient, an injection control module, and a user activated control device coupled to the control module; the control device including an elastic portion with an internal volume compressible by application of an external force to the elastic portion; the control module comprising a pressure sensor in fluid communication with the internal volume of the control device, wherein the internal volume of the control device is included in a closed volume that is separate from and not in fluid communication with the fluid reservoir; and the control module being configured to perform a method comprising the steps of:
sensing an internal pressure of the internal volume of the control device, the internal pressure being greater than a baseline internal pressure, and the internal pressure being in response to the application of the external force to the elastic portion that compresses the internal volume from a first volume to a second volume;
generating an injection control signal based upon the internal pressure;
continuing to sense the internal pressure of the control device after release of the application of the external force and a rebounding of the elastic portion to the first volume; and
generating a notification, if the sensed internal pressure drops below the baseline pressure, after the release of the application of the external force.

19. The system of claim 18, wherein the notification comprises a visual signal.

20. The system of claim 18, wherein the notification comprises an audible signal.

21. The system of claim 18, wherein the notification is indicative of a leak in the closed volume.

* * * * *